United States Patent [19]

Hosoya et al.

[11] Patent Number: 4,799,104
[45] Date of Patent: Jan. 17, 1989

[54] VIDEO SIGNAL PROCESSOR FOR ENDOSCOPE

[75] Inventors: Takamasa Hosoya, Hachioji; Kenji Kimura, Tachikawa, both of Japan

[73] Assignee: Olympus Optical Co., Ltd., Japan

[21] Appl. No.: 132,151

[22] Filed: Dec. 14, 1987

[30] Foreign Application Priority Data

Dec. 19, 1986 [JP] Japan .................. 61-303214
Dec. 22, 1986 [JP] Japan .................. 61-305691
Oct. 22, 1987 [JP] Japan .................. 62-267348

[51] Int. Cl.$^4$ .................. A61B 1/04; A61B 1/06; H04N 7/18
[52] U.S. Cl. .................. 358/98; 128/6; 358/27; 358/28
[58] Field of Search .................. 358/98, 27, 28; 128/6

[56] References Cited

U.S. PATENT DOCUMENTS

| | | | |
|---|---|---|---|
| 4,710,800 | 12/1987 | Fearing | 358/28 |
| 4,716,457 | 12/1987 | Matsuo | 358/98 |
| 4,737,842 | 4/1988 | Nagasaki | 358/27 |
| 4,742,388 | 5/1988 | Cooper | 358/98 |
| 4,746,974 | 5/1988 | Matsuo | 358/98 |

Primary Examiner—Howard W. Britton
Attorney, Agent, or Firm—Ostrolenk, Faber, Gerb & Soffen

[57] ABSTRACT

A video signal processor for endoscope has the functions of converting a picture signal representing an image of a coeloma or the like which is being observed into a television video signal and of externally controlling the tint. The processor includes output means in at least two systems for delivering the television video signal, and tint controlling means for controlling the tint of the television video signal of at least one system independently from the tint of the television video signal of other system.

15 Claims, 11 Drawing Sheets

VIDEO SIGNAL PROCESSOR FOR ENDOSCOPE

FIELD OF THE INVENTION AND RELATED ART STATEMENT

The invention relates to a video signal processor for endoscope, and more particularly, to such processor which converts an image, representing a coeloma observed through an electronic endoscope or fibrescope having a camera element at its distal end and also including an eyepiece assembly located at the proximate end to which a television camera is coupled, into a video signal for delivery to and for use in an external equipment such as a monitoring observation television set or monitoring image recording system.

As is well recognized, a usual television system comprises a television camera and a television receiver, and a video signal processor is contained within the camera. By contrast, a television system for an endoscope comprises an electronic endoscope or an endoscope integrally containing a television camera capable of taking a picture, a video signal processor for converting a camera output signal into a television video signal, and an external equipment such as a monitoring television receiver set or an image recording system which records an image as it is observed.

In the television system for endoscope, a television video signal of high image quality including the color and resolution and comprising an R (red) - G (green) - B (blue) color signal is formed by the video signal processor in order to enable an appropriate diagnosis to be rendered by a physician. One form of such video signal processor used in the prior art is illustrated in block form in FIG. 14. As shown, an electronic endoscope 4, for example, is adapted to be inserted into coeloma, and an imager 5 comprising CCD (charge coupled elements) is disposed at the distal end of the electronic endoscope 4 for receiving an optical image, which is subject to a photoelectric conversion within the imager 5 to provide a picture signal so as to be input to a video signal processor 1 which is disposed outside the coeloma and which is of sequential area type. The input signal is passed through an amplifier 6 to be applied to a preprocessor 7 where high frequency components are eliminated, a gamma correction is applied and a video output signal is clipped to a constant level so that a picture signal of an object being photographed be represented as accurate an electrical signal as possible. Subsequently, R signal is stored in a frame memory 8a, G signal is stored in a frame memory 8b, and B signal is stored in a frame memory 8c, all in synchronism with a timing pulse. The respective color signal is then read out in synchronism with the timing pulse and fed to a post-processor, where a profile is emphasized. A tint controller 10 is connected to an external resistor $V_R$ which establishes a color hue, whereby the gain of R, G and B signals is varied to adjust the tint of an image. Subsequently, the adjusted signals are delivered to output terminals 10a, 10b and 10c as a set of television video signals.

Figure 14:
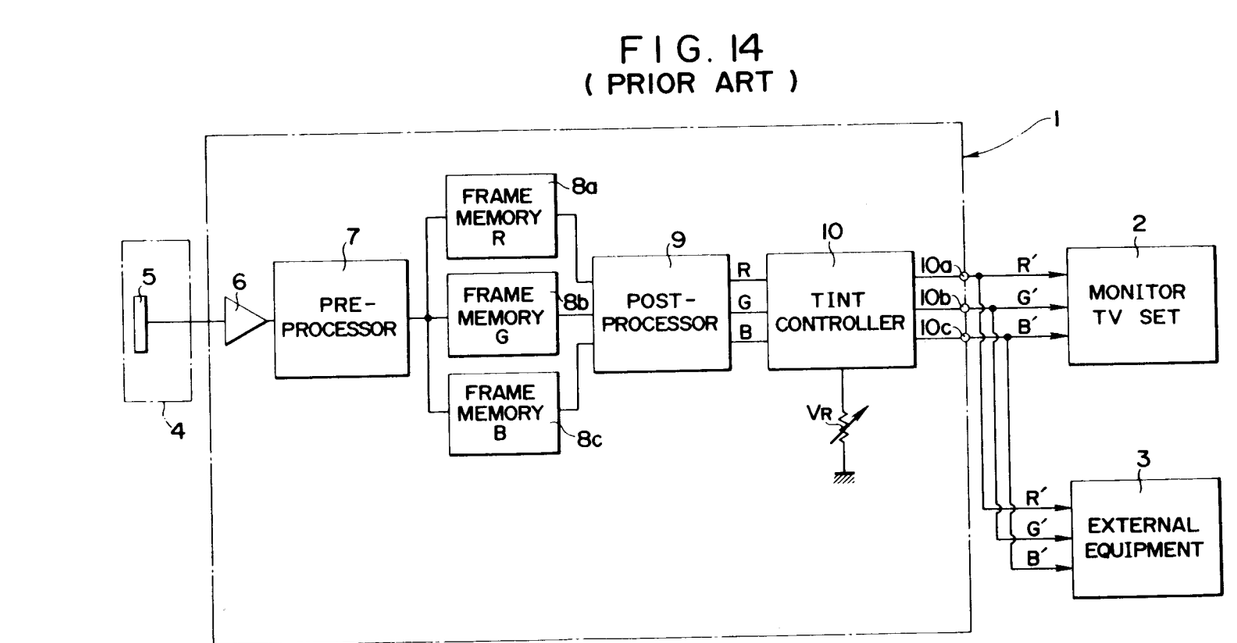
FIG. 14 is a block diagram of an electrical circuit of a conventional video signal processor for endoscope.

A monitor television set 2 which enables an observation by a physician for purpose of diagnosis, a photographic image recording system which makes a record of a picture appearing on the monitor television set, an image processor which determines a characteristic value of an image, a video tape recorder which records an image being observed, a video disc unit, a computer which controls the filing of images or other external equipment 3 are connected to the output terminals 10a to 10c of the video signal processor 1. A set of television video signals comprising R', G' and B' signals having an equal tint are delivered to these external equipments.

In the described video signal processor 1 of the prior art, it will be noted that there is only one tint controller 10, whereby video signal of an equal tint is output to a plurality of external equipments such as the monitor television set 2 or other equipments 3 which are connected to the output terminals 10a to 10c.

However, in the television system for endoscope, a pair of monitor television sets are connected with the output terminals, one being used for observation by a physician for purpose of diagnosis and the other being provided for a photographic recording. Because of a variation in the color rendition from monitor set to set which is inevitable, when a common television video signal having an equal tint is input from the output terminals 10a to 10c, a pair of monitor television set display images of different tints. Since the photographic recording system is designed to provide a faithful color reproduction upon a photograph of an image viewed on the monitor television set thereof, any difference in the color between the pair of monitor television sets results in a difference between the color on the photograph and the color on the observation television set, presenting difficulty in rendering a diagnosis by the physician.

A usual television system for endoscope which employs an electronic endoscope or a fibrescope coupled with an endoscope television camera is arranged to provide video signals corresponding to three primary colors R, G and B in order to improve the image quality including the color and the resolution. However, a commercially available monitor television set has no capability to control the tint of R, G and B video signals. Thus, when one of the monitor television sets of the pair is used according to a composite video signal system (NTSC system), a tint control is enabled in this monitor television set, which however suffers from the degradation in the image quality.

In a practical diagnosis procedure, a physician frequently operates a user's tint control of the video signal processor to change the colors appearing on the observation monitor television set to his preferred colors or colors which are appropriate for the purpose of diagnosis, depending on the variety of objects being observed. This also changes the tint of input signals to an external equipment such as an image processor which is connected to the same output terminals in addition to the monitor television set. A change in the signal representing the colors also has adverse influences upon various determinations. By way of example, when the extent of a lesion is continuously determined according to a difference in the color, measured data obtained before and after a change in the tint would be discontinued, presenting a problem that such data does not exhibit the objectivity.

On the other hand, in the television system for endoscope, the tint of an image appearing on the monitor television set has been controlled in a number of ways in order to achieve a faithful reproduction of original colors produced in an image being observed on the monitor television set, in a manner mentioned below:

(1) A picture of an object is taken in white color through a television camera and the white color is reproduced by a manual operation of tint controlling knob on the video signal processor or the monitor television set in order to adjust the tint;

(2) Or where the video signal processor has the capability to adjust the white color automatically, a picture is taken in the white color, and the resulting output signal fed to the monitor television set is controlled to a given signal.

As to a tint control in the monitor television set, (1) such control is not available in a system which employs a composite video signal of PAL type or RGB video signals since a commercially available product for a monitor television set does not allow an external tint control;

(2) a color matching is performed in a system which employs a composite video signal of NTSC type, by delivering color bars on the monitor television set.

However, when a user attempts a color matching, if an object being observed represents a chart in white color and a user achieves a white balance while viewing an image appearing on the monitor television set, he will tend to achieve the control according to his memory, resulting in a change in the white color from individual to individual;

(2) where the automatic white color control function of the video signal processor is utilized, such control is unavailable for RGB and PAL type and accordingly the individual monitor television sets have a variation in the tint from set to set. Hence, if a given signal is delivered from the video signal processor, the resulting tint will be different in the individual monitor television set. For an adjustment of the monitor television set of NTSC type utilizing color bars, each user achieves such adjustment according to his own memory, again resulting in a variation in the achieved matching of color bars from individual to individual.

In summary, a faithful reproduction of colors of an object being observed could not have been accomplished in a television system for endoscope. Accordingly, in a diagnosis utilizing an electronic endoscope, physicians have evaluated the colors according to their respective standards, resulting in an inconvenience that an agreement could not be reached between results of diagnosis among such physicians when they exchange their information. A comparative evaluation between different physicians have also been inhibited or of no significance since colors differ for a common data in the processing of images.

OBJECT AND SUMMARY OF THE INVENTION

It is a first object of the invention to provide a video signal processor for endoscope which eliminates inconveniences experienced in a conventional television system for endoscope as mentioned above and which permits the tint to be adjusted at will.

It is a second object of the invention to provide a video signal processor for endoscope which eliminates a variation in the color appearing on the screen of the monitor television set which results from a variation in the preference from observer to observer and which is capable of automatically achieving a faithful reproduction of colors of the object being observed on the screen of the monitor television set.

In accordance with the invention, an arrangement is provided to permit the tint from a video signal system which is delivered at a plurality of output terminals after conversion into a television video signal, to be independently adjusted either internally or externally or both. This brings forth the following advantages.

(A) The tint of the monitor television set can be maintained the same as that of a television set used within an image recording system without causing a degradation in the image quality, thus permitting a photograph to be taken in the same color as that observed on the monitor television set.

(B) An output signal to an external equipment such as the image recording system or the image processor can be separate and independent from the signal fed to the monitor television set which is used for purpose of observation, and accordingly such output signal is not influenced by any change in the tint of the monitor television set performed by a physician, allowing an objective determination of the extent of a lesion according to a difference in the tint.

(C) The color in the monitor television set can be changed independently from the color used in the television set disposed within the image recording system, enabling an intensional change in the tint on the photograph from that of the monitor television set.

(D) Since a faithful reproduction of the color of a designated color chart is enabled on the screen of the monitor television set, the colors of an object being photographed can be faithfully reproduced on the screen of the monitor television set in practical use without requiring any manual intervention since such reproduction is achieved through a feedback loop.

(E) There is no variation in the color from monitor television set to set or from individual to individual. Accordingly, every physician is permitted to view the resulting image in the same color for purpose of diagnosis, and an objective evaluation of data obtained as a result of the processing of an image by all the physicians can be made. In this manner, the disadvantages of the prior art as mentioned above are eliminated by providing an improved video signal processor for endoscope.

DETAILED DESCRIPTION OF PREFERRED EMBODIMENTS

Figure 1:
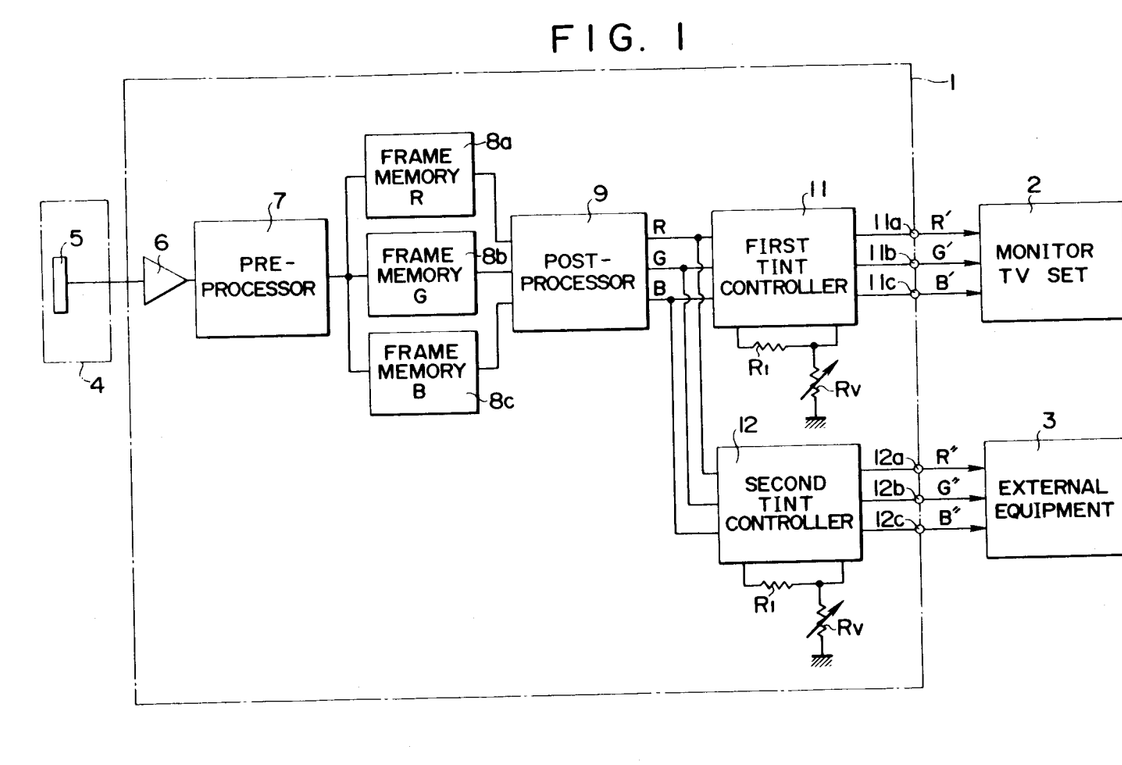
FIG. 1 is a block diagram of an electrical circuit used in a video signal processor for endoscope according to a first embodiment of the invention.
Figure 2:
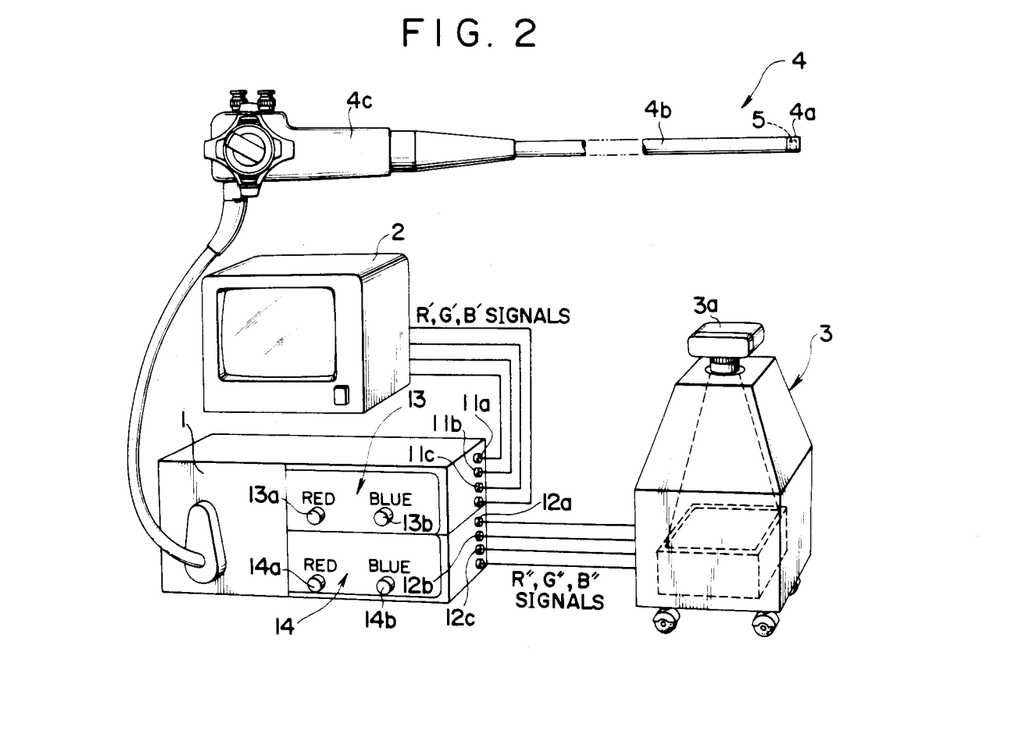
FIG. 2 is a schematic view of a television system for endoscope including the video signal processor having the electrical circuit shown in FIG. 1.
Figure 3:
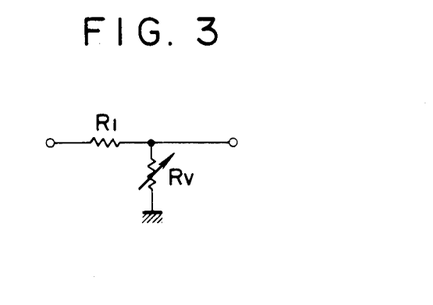
FIG. 3 is a circuit diagram of one form of a tint controller used in FIGS. 1 and 2.

FIGS. 1 to 3 illustrate a video signal processor according to a first embodiment of the invention which is applied to an electronic endoscope. To avoid a repeated description, parts similar to those shown in the conventional arrangement illustrated in FIG. 14 are designated by like reference numerals and characters. As before, a video signal processor 1 includes a post-processor 9 which delivers R, G and B signals, which are fed to a first tint controller 11 and a second tint controller 12 which are connected in parallel to each other to the processor 9. The first tint controller 11 includes output terminals 11a, 11b and 11c, delivering R', G' and B' signals, respectively, which are fed to a monitor television set 2 connected to these output terminals. The second tint controller 12 includes output terminals 12a, 12b and 12c, delivering R", G" and B" signals, which are delivered to a variety of external equipments 3 such as an image recording system, a video image recording system or the like which are connected to the terminals 12a to 12c.

FIG. 2 is a schematic illustration of a television system for endoscope including the video signal processor having the electrical circuit shown in FIG. 1. A distal end 4a of the electronic endoscope 4 has an imager 5, comprising CCD elements, disposed therein, which delivers a signal to the video signal processor 1 through lead wires passing through an intermediate length 4b of the endoscope which is adapted to be inserted into a coeloma and also through a proximate operator 4c. The video signal processor 1 has a front panel including a first operating panel 13 and a second operating panel 14. Knobs 13a, 14a which increase or decrease the strength of R signal as referenced to G signal are disposed on the panel 13 while knobs 13b, 14b which increase or decrease the strength of B signal are disposed on the panel 14. Outputs adjusted by the knobs 13a, 13b on the first operating panel 13 are applied to the input terminal of the monitor television set 2 as R', G' and B' signals while outputs adjusted by the knobs 14a, 14b on the second operating panel 14 are applied to the input terminal of an external equipment 3 such as an image recording system including a photographic camera 3a as R", G" and B" signals. FIG. 3 shows one form of a circuit associated with either knob 13a to 14b. As shown, the circuit comprises a resistive voltage divider formed by a resistor R1 and a variable resistor Rv.

A television video signal which is delivered from the post-processor 9 of the video signal processor 1 is fed through the first tint controller 11 to be displayed on the monitor television set 2. By operating the knobs 13a, 13b on the first operating panel 13, the tint can be adjusted. The television video signal from the post-processor 9 is also fed through the second tint controller 12 to be applied to the external equipment 3, and the tint can be controlled by operating the knobs 14a, 14b on the second operating panel 14. In this manner, a user is free to adjust the tint of two systems independently from each other. Accordingly, (a) the color on the monitor television set can be adjusted to the same color on a monitor television set which is used within the image recording system, without using a monitor television set of NTSC type which causes a degradation in the image quality. (b) The picture signal fed to the monitor television set 2 can be changed to any desired tint preferred by a physician for his observation while the picture signal fed to the external equipment 3 can maintain a consistent tint, providing a record which enables an objective determination.

Figure 4:
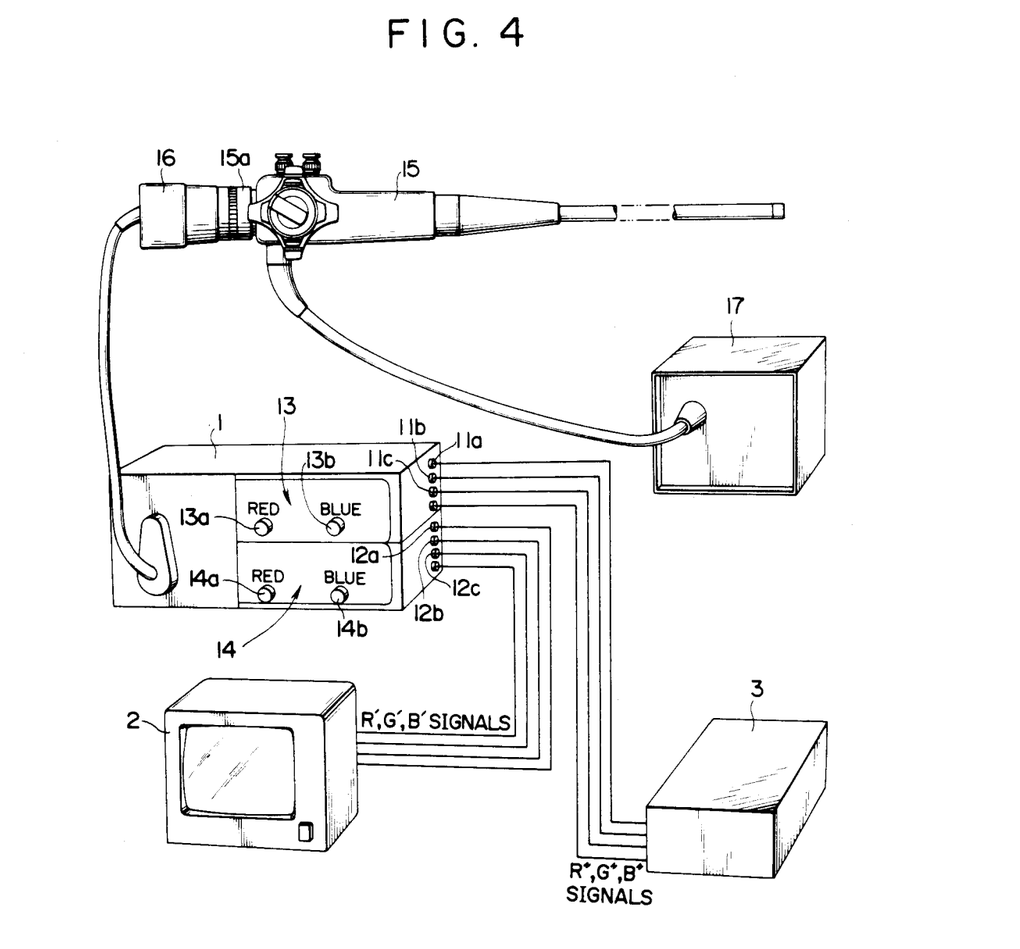
FIG. 4 is a schematic illustration of a television system for endoscope including the video signal processor when used with a fibrescope.

While the electronic endoscope 4 has been used to observe an image in the first embodiment, an endoscope such as a fibrescope may be used for the television system as illustrated in FIG. 4. Thus, a fibrescope 15, which is constructed in a known manner in itself, includes an eyepiece assembly 15a, to which a television camera 16 for endoscope is coupled, and a picture signal from the camera 16 is fed to the video signal processor 1 which is constructed in the same manner as illustrated in FIG. 1. The processor 1 includes one set of output terminals 11a to 11c which are connected to an external equipment 3 such as an image recording system or an image processing system, and also has another set of output terminals 12a to 12c which are connected to a monitor television set 2. A light source assembly 17 is connected to a light guide of the fibrescope 15. The tint in the two systems can be independently adjusted by the tint controllers 11 and 12 mentioned above.

Figure 5:
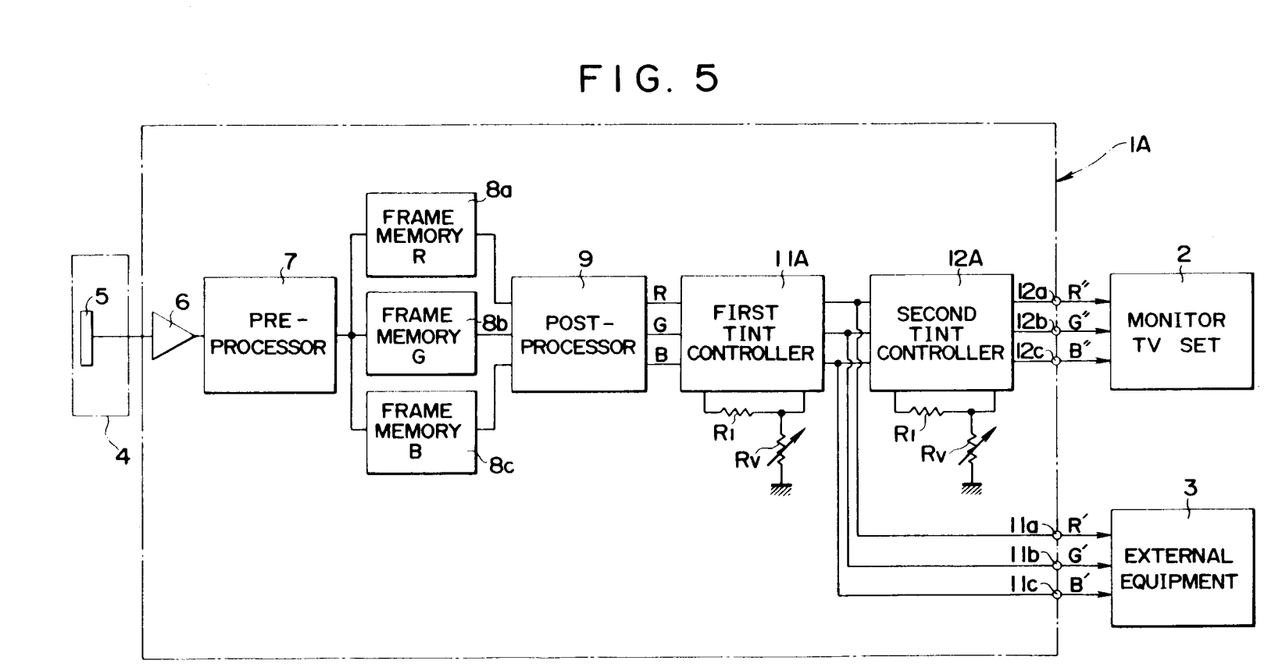
FIGS. 5 and 6 are block diagrams of electrical circuits of video signal processors for endoscope according to a second and a third embodiment of the invention.

FIG. 5 shows a second embodiment of the invention. Specifically, in contrast to the first embodiment in which the first and the second tint controllers 11 and 12 are connected in parallel to each other, a video signal processor 1A includes a pair of tint controllers 11A, 12A which are connected in series. Specifically, the first tint controller 11A is connected to the output of the post-processor 9, and the output of the first tint controller 11A is connected to the input of the second tint controller 12A and also connected to a set of output terminals 11a to 11c. The output of the second tint controller 12A is connected to another set of output terminals 12a to 12c. One set of output terminals 11a to 11c may be connected to an external equipment 3 while another set of output terminals 12a to 12c may be connected to a monitor television set 2. By operating a knob to a given position to adjust a resistor Rv of the first tint controller 11A, a user is able to control the tint. A knob on the second tint controller 12a is also adjusted by a user to adjust a resistor Rv, again for controlling the tint, thus achieving a color matching on the monitor television set 2. When color adjustments are once made in this manner, it is possible that the knob on the first tint controller 11A may be operated by the preference of the physician or depending on the location of a site to be observed, thus permitting a free change in the color of the both units. A click stop position may be defined in association with the knob on the first tint controller 11A so that a reference condition may be readily established.

Figure 6:
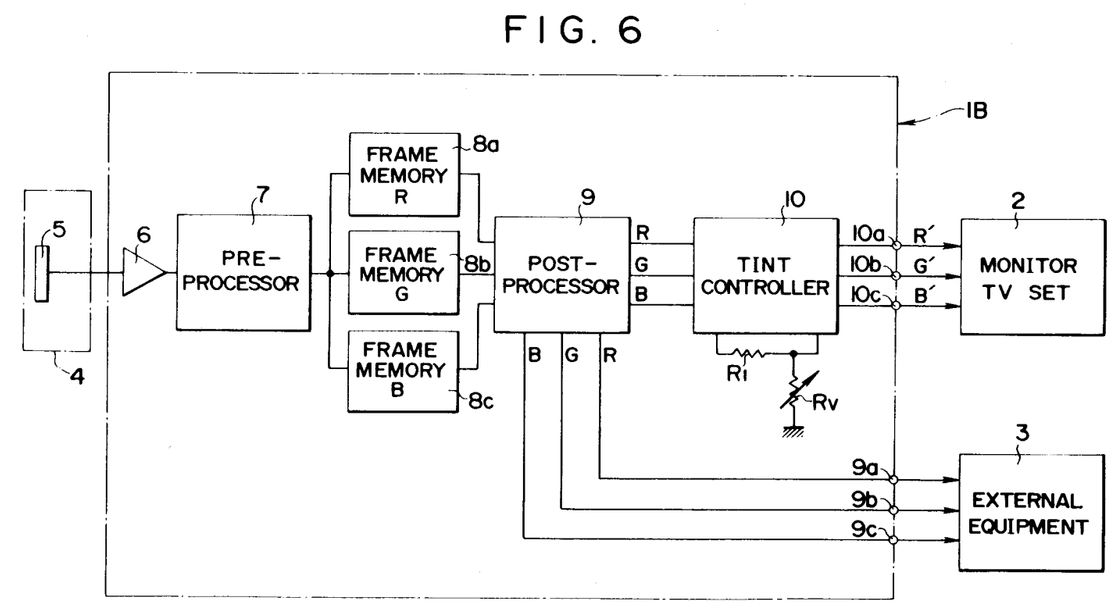

FIG. 6 shows a third embodiment of the invention, specifically illustrating a video signal processor 1B including a post-processor 9 which deliver one set of R, G and B output signals directly delivered to a set of output terminals 9a to 9c without passing through any tint controller to feed an external equipment 3 such as an image recording system which is connected to the output terminals 9a to 9c. A monitor television set 2 is connected to another set of output terminals 10a to 10c, to which the R', G' and B' signals which have been controlled by a tint controller 10 is delivered. In this manner, a set of output signals from the video signal processor 1B which is not adjusted is applied to a monitor television set used within the external equipment 3 while another set of output signals, the tint of which can be freely adjusted by an operator, is applied to the monitor television set 2 for display, achieving a similar effect as in the first embodiment.

Figure 7:
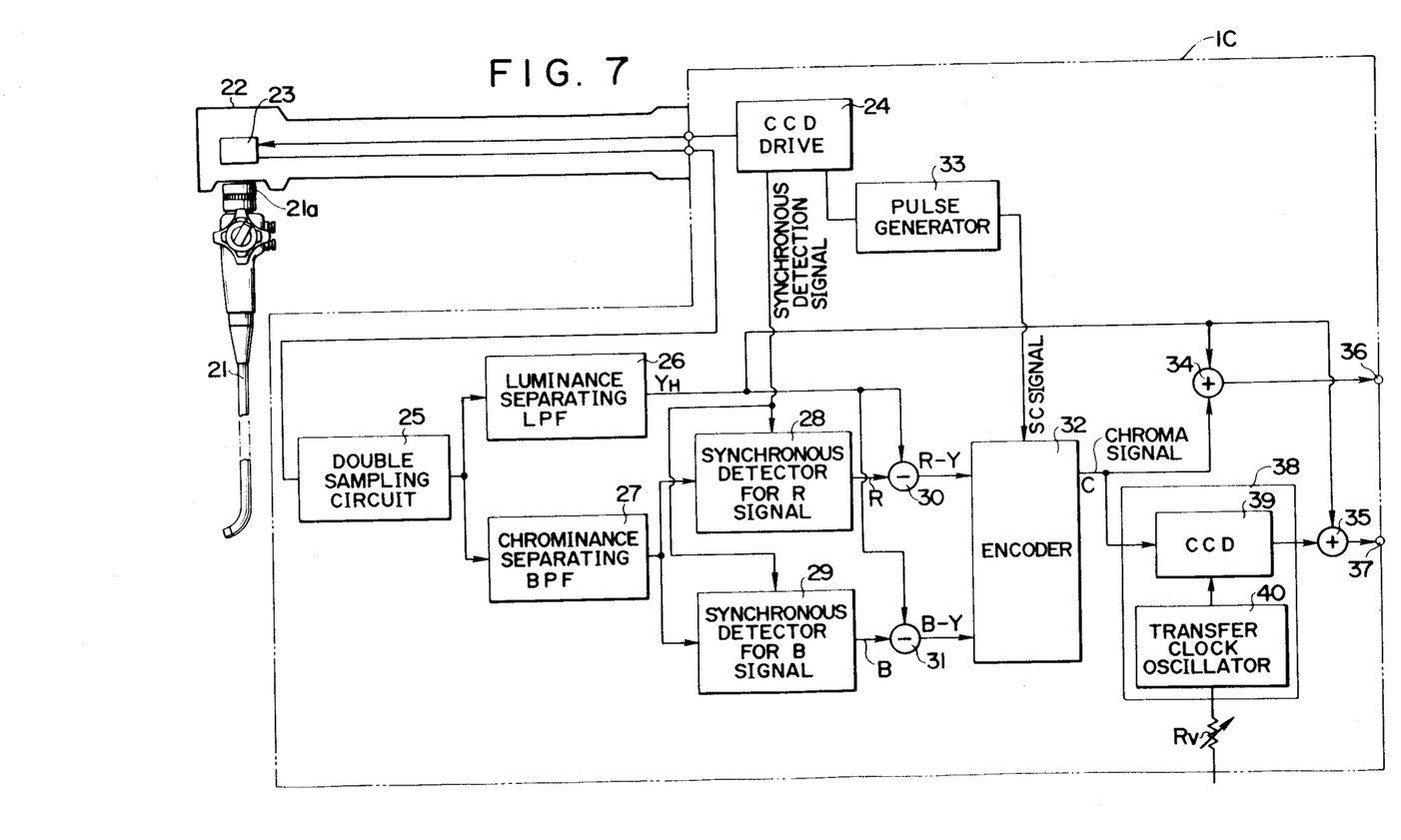
FIG. 7 is a block diagram of an electrical circuit of a video signal processor for endoscope according to a fourth embodiment of the invention which is applied to a television system of mosaic color filter type.

FIG. 7 is a block diagram of a video signal processor according to a fourth embodiment of the invention. The first to the third embodiment have been the application of the invention to a television system of an area sequential type. However, the present embodiment represents the application of the invention to a television system for endoscope which is of mosaic color filter type, also referred to as simultaneous color type.

In a video signal processor 1C according to this embodiment, a television camera 22 of a mosaic color filter type is attached to the eyepiece 21a of a fibrescope 21, thereby providing a picture signal of an image being observed. The camera 22 includes an imager 23 comprising CCD elements and driven by a CCD drive circuit 24, delivering a picture signal which is input to a double sampling circuit (CDS) 25. An output from the double sampling circuit 25 is fed to a low pass filter 26 having the function to separate a luminance signal and also to a bypass filter 27 having the function to separate a chrominance carrier. An output from the bypass filter 27 is then fed to a pair of synchronous detectors 28, 29 which detects R and B signals, respectively. The R and B signals from the detectors are applied to subtractors 30 and 31, respectively, together with the luminance signal $Y_H$, deriving color difference signals R-Y and B-Y which are fed to an encoder 32, which functions to form a composite video signal. A subcarrier signal SC is applied to the encoder 32 from a pulse generator 33. The encoder 32 delivers a chroma signal C, which is applied to a pair of adders 34 and 35 together with the luminance signal $Y_H$. The purpose of the adders 34 and 35 is to constitute two systems of output means which derive a pair of television video signals, which are output on output terminals 36 and 37, respectively. Thus, a monitor television set 2 which is used for purpose of observation and an external equipment 3 are connected to the output terminals 36 and 37, respectively.

In the present embodiment, a tint controller 38 is connected in at least one of video signal systems of the video signal processor. The tint controller 38 is formed by a hue controlling variable phase shifter comprising a delay circuit 39 formed by CCD elements and an oscillator 40 which develops transfer clocks. The oscillation frequency of the oscillator 40 is controlled by a variable resistor Rv which adjusts the tint thereby controlling the phase of the chroma signal for purpose of controlling the tint.

In the embodiment shown in FIG. 7, a picture signal is obtained from the television camera 22 coupled to the fibrescope 21, but it should be understood that the picture signal may be derived from the electronic endoscope as well.

In the first to the fourth embodiment described above, the video signal processor includes a tint controller therein. However, a tint controller may be defined as an adaptor for an external connection to a video signal processor for purpose of controlling a tint as will be described below in connection with a fifth embodiment.

Figure 8:
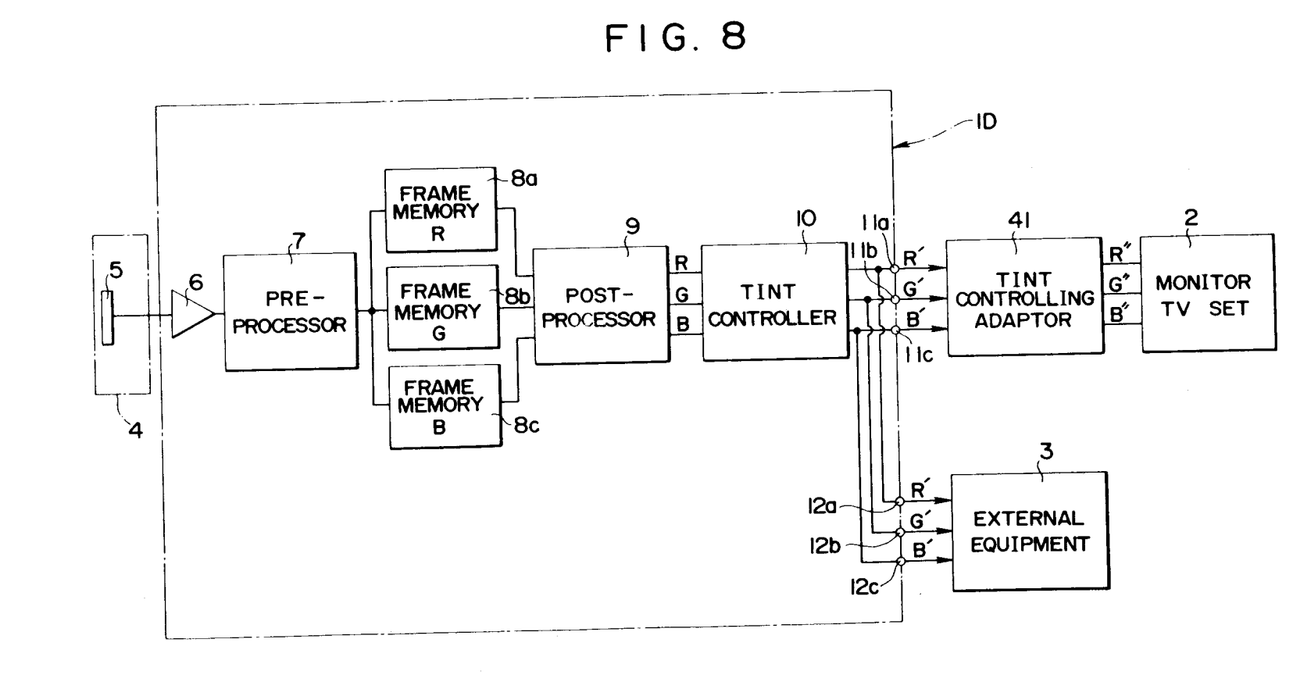
FIG. 8 is a block diagram of an electrical circuit of a video signal processor for endoscope according to a fifth embodiment of the invention.
Figure 9:
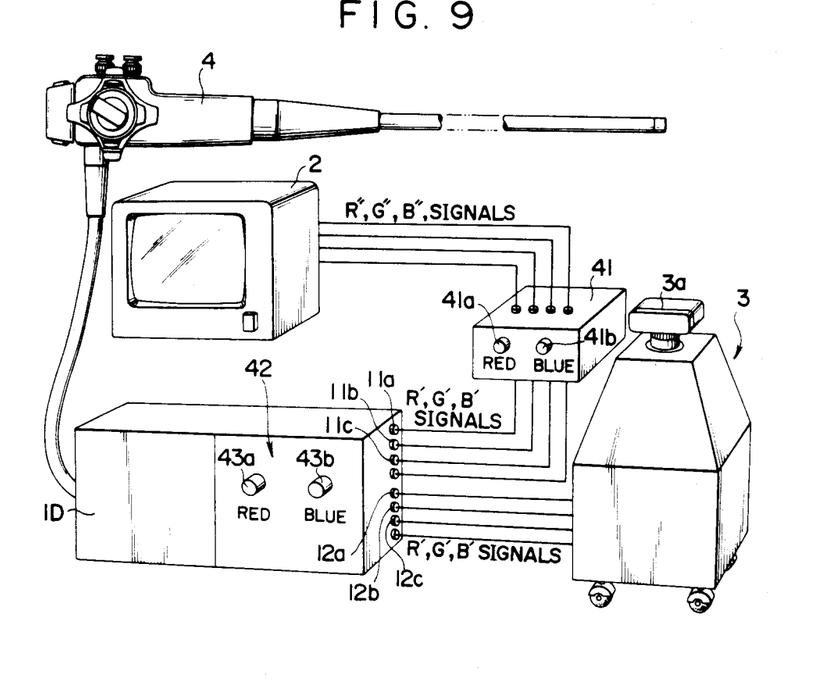
FIG. 9 is a schematic illustration of a television system for endoscope including the video signal processor having the electrical circuit shown in FIG. 8.
Figure 10:
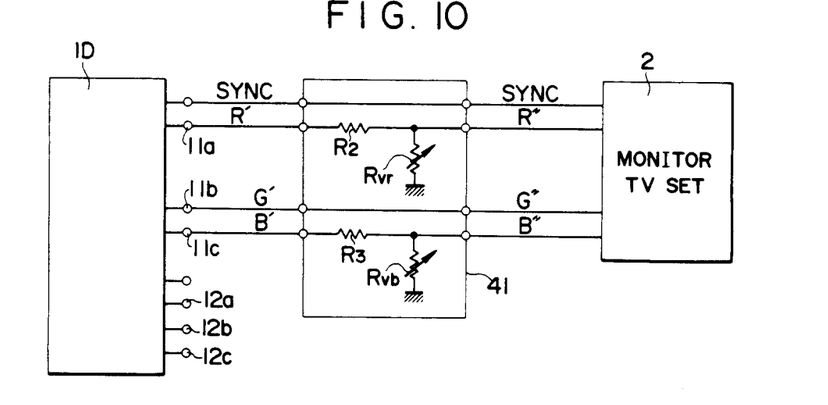
FIG. 10 is a circuit diagram of a tint controlling adaptor shown in FIGS. 8 and 9.

The fifth embodiment is illustrated in FIGS. 8, 9 and 10. As shown in FIG. 8, a video signal processor 1D includes a single tint controller 10 which has its outputs connected to a set of output terminals 11a to 11c and also to another set of output terminals 12a to 12c. A tint controlling adaptor 41 which functions in the same manner as the tint controller 10 mentioned above may be connected to one set of output terminals 11a to 11c, for example, and the output terminals of the adaptor 41 may be connected to a monitor television set 2. An external equipment such as an image recording system may be connected to the set of output terminals 12a to 12c.

FIG. 9 shows a television system for endoscope which includes the video signal processor 1D having the electrical circuit shown in FIG. 8 and the adaptor 41. A picture signal is supplied from the electronic endoscope 4 to the video signal processor 1D, which has a front panel 42 on which a pair of knobs 43a and 43b are disposed for increasing or decreasing the strength of R and B signals, respectively, as referenced to G signal. Outputs from the video signal processor, the tint of which is adjusted by means of the knobs 43a and 43b, are delivered as R', G' and B' signals to be applied to the sets of output terminals 11a to 11c and 12a to 12c. Accordingly, the tint of the external equipment 3 connected to the set of output terminals 12a to 12c is controlled in accordance therewith.

On the other hand, the adaptor 41 is connected to the set of output terminals 11a to 11c, and has an electrical circuit, one form of which is illustrated in FIG. 10. Specifically, a combination of a resistor R2 and a variable resistor Rvr is effective to adjust the gain of R signal system as referenced to G signal, and a combination of a resistor R3 and a variable resistor Rvb is effective to adjust a gain of B signal system. On its front surface, the adaptor 41 is provided with a pair of knobs 41a and 41b, which are effective to adjust variable resistors Rvr and Rvb, respectively, as illustrated in FIG. 9. Accordingly, by operating the knobs 41a and 41b, the tint of the monitor television set 2 can be controlled.

In operation, the knobs 43a and 43b are initially operated to control the tint of the external equipment 3 by means of the tint controller 10 located within the video signal processor 1D. The knobs 41a and 41b on the adaptor 41 may then be adjusted to control the tint of the monitor television set 2 to any desired color, thus achieving a similar effect as achieved in the second embodiment shown in FIG. 5. The adaptor 41 of the present embodiment may be connected to a video signal processor which is not provided with any tint controller to enable a tint control of a television video signal which is input to a monitor television set or an external equipment which is connected to the video signal processor.

Figure 11:
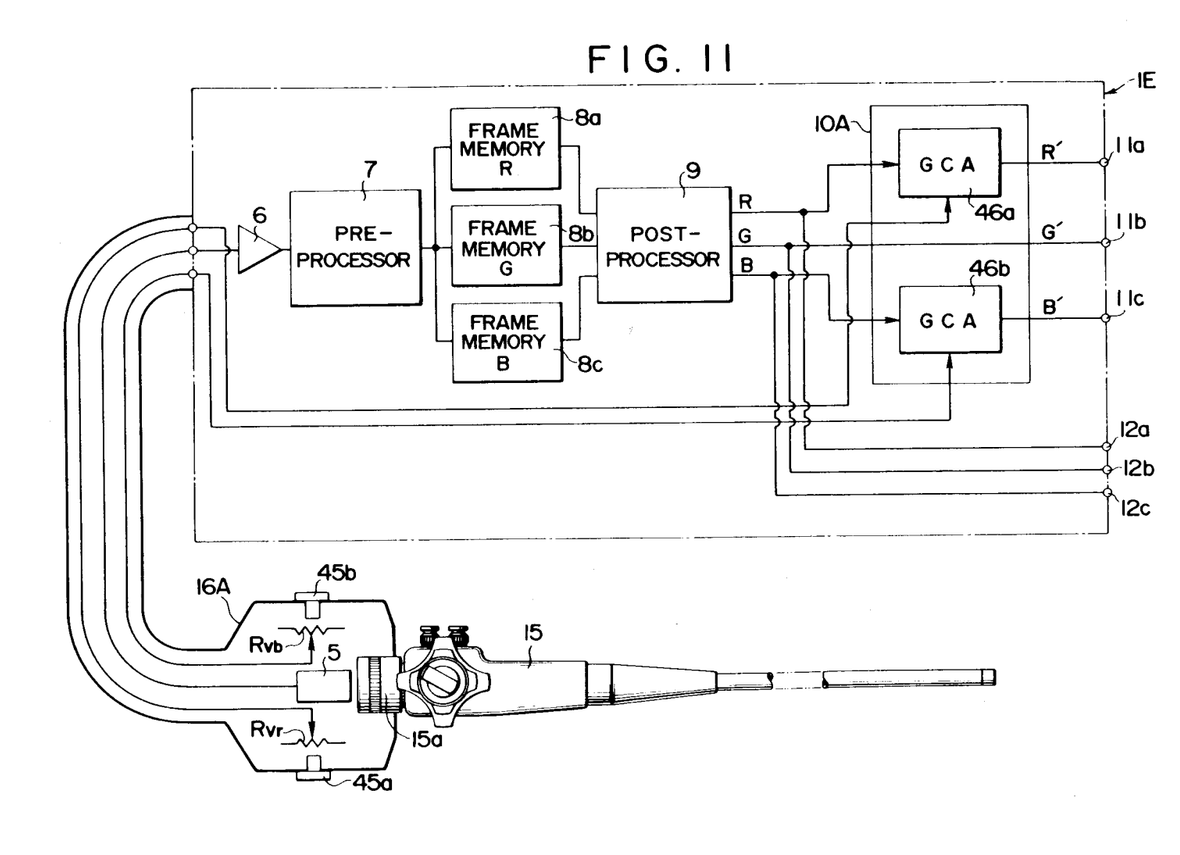
FIG. 11 is a block diagram of an electrical circuit of a video signal processor for endoscope according to a sixth embodiment of the invention.

FIG. 11 shows a video signal processor 1E according to a sixth embodiment of the invention which includes a single tint controller 10A, the tint control of which is performed by means of knobs 45a, 45b which are provided on the part of a television camera 16A for endoscope. As mentioned before in connection with FIG. 4, when obtaining a picture signal of an image being observed using a fibrescope 15, the television camera is coupled to the eyepiece 15A of the fibrescope 15 so that a picture signal may be derived from an imager 5 such as formed by CCD elements placed therein. Accordingly, an ease of operation is greatly enhanced by disposing tint controlling members on the television camera.

In this embodiment, the television camera 16A coupled to the eyepiece 15A of the fibrescope 15 in a manner illustrated in FIG. 11 contains a variable resistor Rvr which adjusts a gain of R signal system as referenced to G signal and another variable resistor Rvb which adjusts a gain of B signal system as referenced to G signal. These variable resistors can be adjusted by means of operating knobs 45a, 45b which are exposed externally of the camera 16A. These variable resistors Rvr, Rvb are effective to adjust the gain of R and B signal systems in the tint controller 10A which are formed by a pair of gain controlled amplifiers 46a, 46b which are disposed within the video signal processor 1E. It will be noted that in the processor 1E shown in FIG. 11, part of R, G and B output signals from a post-processor 9 are directly delivered to a set of output terminals 12a to 12c without passing through the tint controller 10A.

Figure 12:
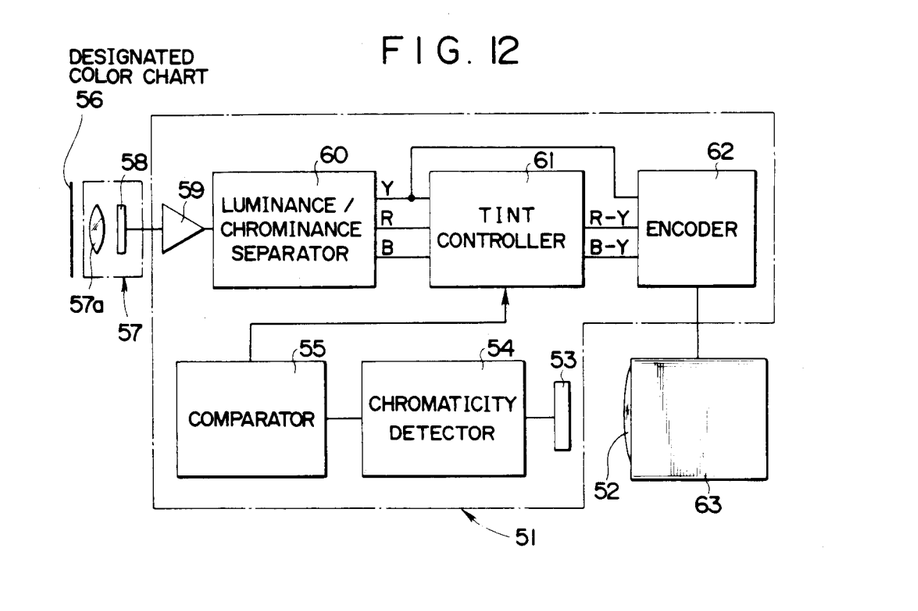
FIG. 12 is a block diagram of an electrical circuit of a tint controller used in a video signal processor for endoscope according to a seventh embodiment of the invention.
Figure 13:
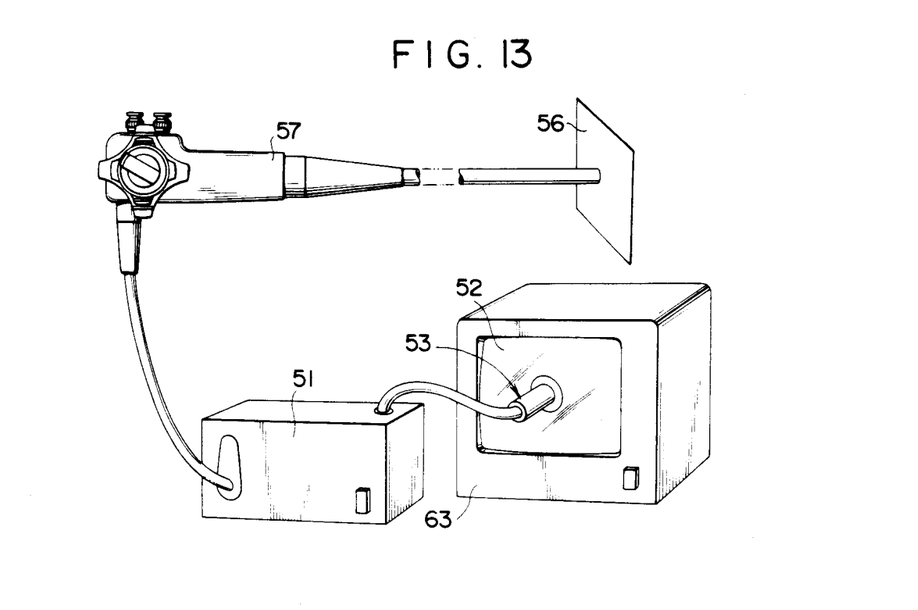
FIG. 13 is a perspective view of a television system for endoscope including the tint controller shown in FIG. 12.

FIGS. 12 and 13 illustrate a video signal processor according to a seventh embodiment of the invention. This embodiment is constructed to accomplish the second object of the invention, and at this end, a video signal processor 51 includes a chromaticity detector 54 and a comparator 55. The chromaticity detector 54 is connected to receive an output from an R, G and B sensor 53 which is mounted on the screen 52 of a monitor television set at a location where a colorimetry is possible for detecting light components of R, G and B signals. The comparator 55 includes a chromaticity on a designated color chart 56, to be described later, previously established therein, and compares the chromaticity of the designated color chart 56 as determined by the electronic endoscope 57 against this chromaticity, thereby providing a feedback of a difference signal of that chromaticity to a tint controller 61.

An electronic endoscope 57 which is adapted to be inserted into coeloma receives a reflection from the designated color chart 56 as an object being observed, through an imager 58 comprising CCD elements through an objective lens 57a. The imager 58 performs a photoelectric conversion of the signal to feed the video signal processor 51. In the processor 51, this signal is amplified by an amplifier 59, and is then applied to a luminance/chrominance separation circuit 60 such as a filter, which separately deliver a luminance signal Y and R and B signals. These output signals are then converted into a pair of color difference signals R-Y and B-Y by the tint controller 61, and the resulting color difference signals are input to an encoder 62 together with the signal Y for forming a composite video signal (NTSC) to be delivered to a monitor television set 63.

In operation, the designated color chart (single color) 56 is photographed by the CCD imager 58 located at the distal end of the electronic endoscope 57, and the resulting picture signal is input to the amplifier 59 of the video signal processor 51. After the amplification, the picture signal is separated into the luminance signal Y and the color signals R and B by the separation circuit 60, and the resulting signals are applied to the tint controller 61. The tint controller 61 forms the color difference signals R-Y and B-Y, which are fed to the encoder 62 together with the Y signal to be encoded into a composite video signal of NTSC type to be delivered to the monitor television set 63. Accordingly, the television set 63 displays an image of the designated color chart 56 on the screen 52. The light components of R, G and B of the image of the chart 56 are detected by the RGB sensor 53 and are fed to the chromaticity detector 54. The chromaticity detector 54 calculates the chromaticity, which is then supplied to the comparator 55. The comparator 55 compares the calculated chromaticity against the preset chromaticity and determines a difference signal in the chromaticity, which is fed back to the tint controller 61 so that the tint may be changed to establish the same chromaticity as that preset in the comparator. While the above description covers a composite video signal of NTSC type, the same applies to R, B and G signals.

It will be understood that rather than employing a closed loop arrangement as mentioned above, the chromaticity difference signal which is fed back to the tint controller 61 from the comparator 55 may operate upon an instrument which provides an analog or digital display, thereby allowing an operator to perform a manual adjustment by means of a variable resistor which is externally coupled to the tint controller 61. While the electronic endoscope has been employed in the embodiment mentioned, an endoscope which incorporates a fibrescope may also be utilized, by disposing a television camera in close contact with the eyepiece of the endoscope to derive an output from the camera to the video signal processor.

What is claimed is:

1. A video signal processor for endoscope comprising
means for converting a picture signal of an image being observed such as that of a coeloma into a television video signal;
output means in at least two systems for delivering the television video signal from the converting means;
and tint controlling means for allowing the tint of the television video signal of at least one system to be controlled either internally or externally and independently from the tint of the other system.

2. A video signal processor according to claim 1 in which said means for converting a picture signal into a television video signal comprises an imager such as formed by solid state camera element receiving an image of a coeloma or the like which is being observed and providing a photoelectric conversion of the image, an amplifier for amplifying an output from the imager, a pre-processor which provides the elimination of high frequency components from an output signal of the amplifier, a gamma correction and a clipping of a video output signal to a given level, a plurality of frame memories for storing R, G and B signals from the pre-processor in synchronism with a timing pulse, and a post-processor for performing a profile emphasis of each color signal read from the respective frame memories in synchronism with the timing pulse.

3. A video signal processor according to claim 1 in which said means for converting a picture signal into a television video signal comprises an imager such as formed by a solid state camera element for receiving an image of a coeloma or the like which is being observed and effecting a photoelectric conversion thereof, a double sampling circuit for receiving an output from the imager, a combination of a low pass filter which separates a luminance signal and a bypass filter which separates a chrominance carrier, each of the filters being fed with an output from the double sampling circuit, a pair of synchronous detectors receiving an output from the bypass filter and also receiving a synchronizing signal from an imager drive circuit to detect an R signal and a B signal, respectively, a subtractor for subtracting a luminance signal Y obtained by the low pass filter from each of the R signal and the B signal obtained from the respective synchronous detectors to form a pair of color difference signals R-Y and B-Y, an encoder for forming a chroma signal in response to the color difference signals R-Y and B-Y and a subcarrier signal from a pulse generator, and an adder for adding chroma signal from the encoder and a luminance signal to form a television video signal.

4. A video signal processor according to claim 1 in which the tint controlling means comprises a plurality of tint controllers which receive the television video signal from the converting means, each of the tint controller having a color hue established therein and controlling the tint of an image by changing the gain of each color signal component.

5. A video signal processor according to claim 4 in which an output from each of the tint controller is supplied to a corresponding output terminal.

6. A video signal processor according to claim 1 in which the tint controlling means includes a first tint controller receiving the television video signal from the converting means, and a second tint controller receiving an output from the first tint controller, the first and the second tint controller having color hues established therein so as to change the gain of each color signal component to control the tint of an image.

7. A video signal processor according to claim 6 in which an output from the first tint controller is supplied to a first output terminal while an output from the second tint controller is supplied to a second output terminal.

8. A video signal processor according to claim 1 in which the output means comprises an output terminal to which an output from the tint controller is derived, the tint controller receiving the television video signal from the converting means and said output being a tint controlled version of the video signal, and another output terminal to which the television video signal from the converting means is directly supplied.

9. A video signal processor according to claim 8 in which the tint controller is formed by a hue controlling, variable phase shifter comprising a delay circuit formed by CCD elements and an oscillator which develops a transfer clock, the oscillation frequency of the oscillator being controlled by a tint controlling, variable resistor, whereby the phase of a chroma signal is controlled to control the tint.

10. A video signal processor according to claim 1 in which the tint controlling means comprises a tint controlling adaptor connected to one system of the output means to receive the television video signal and controlling the tint of the signal for providing a output.

11. A video signal processor according to claim 10 in which the adaptor comprises a resistive voltage divider for controlling the gain of R signal system and B signal system as referenced to G signal.

12. A video signal processor for endoscope comprising
a television camera for endoscope which is mounted on an eyepiece of a fibrescope for providing a picture signal representing an image of a coeloma or the like which is being observed;
means for converting the picture signal into a television video signal;
output means in at least two systems for delivering the television video signal;
tint controlling means for controlling the tint of the television video signal of at least one system of the output means independently from the tint of the television video signal of the other system;
and means for disposing a tint controlling resistor of the tint controller on the television camera so as to be externally adjusted.

13. A video signal processor according to claim 12 in which the tint controller comprises a gain controlled amplifier for adjusting the gain of R signal system as referenced to G signal in accordance with the tint controlling resistor, and another gain controlled amplifier for adjusting the gain of B signal system in accordance with the tint controlling resistor.

14. A video signal processor for endoscope comprising
an object being photographed which comprises a designated color chart;
a chromaticity detector for taking a picture of the object, for displaying it on a monitor television set and for detecting color information of the image;
a comparator for comparing the color information detected by the chromaticity detector against color information of the object which is previously stored;
and a tint controller responsive to a chromaticity difference signal from the comparator for modulating the video signal so as to remove a difference between color information.

15. A video signal processor according to claim 14 in which color information which is supplied to the chromaticity detector is derived by R, G and B sensor mounted on the screen of a monitor television set for detecting light components of R, G and B signals.

* * * * *